United States Patent

Eder et al.

[11] 3,976,701
[45] Aug. 24, 1976

[54] PROCESS FOR THE PREPARATION OF 9,10-SECOESTRANE DERIVATIVES

[75] Inventors: Ulrich Eder; Gregor Haffer; Jürgen Ruppert; Gerhard Sauer; Rudolf Wiechert, all of Berlin, Germany

[73] Assignee: Schering Aktiengesellschaft, Berlin & Bergkamen, Germany

[22] Filed: Oct. 24, 1973

[21] Appl. No.: 409,234

[30] Foreign Application Priority Data
Oct. 25, 1972 Germany............................ 2253088

[52] U.S. Cl............................ 260/611 A; 260/613 R; 260/611 F; 260/618 H; 260/618 F; 260/346.2 M; 260/590 FA; 260/479 R; 260/469; 260/514 R; 260/340.5; 260/340.7; 260/338; 260/456 R; 260/586 F
[51] Int. Cl.²............................................ C07C 43/20
[58] Field of Search ........ 260/613 R, 618 H, 618 F, 260/611 A, 611 F

[56] References Cited
UNITED STATES PATENTS

| | | | |
|---|---|---|---|
| 3,565,958 | 2/1971 | Los ................................ | 260/613 R |
| 3,658,847 | 4/1972 | Fried................................ | 260/613 |
| 3,714,195 | 1/1973 | Marinus ........................ | 260/613 R |

*Primary Examiner*—Bernard Helfin
*Attorney, Agent, or Firm*—Millen, Raptes & White

[57] ABSTRACT
6,9-Oxido-9,10-seco-1,3,5(10),6,8,14-estrahexaenes, useful as intermediates in the total synthesis of steroids, of the formula

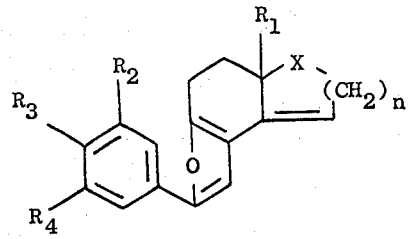

wherein $n$ is 1 or 2, $R_1$ is lower-alkyl, $R_2$, $R_3$ and $R_4$ are H, alkoxy or acyloxy, X is a free or ketalized keto or free, esterified or etherified hydroxymethylene, are produced by the cyclization, with an acid catalyst, of a 9,10-secoestrane of the formula

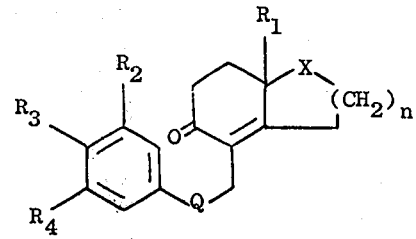

wherein $R_1$, $R_2$, $R_3$, $R_4$, X and $n$ have the values given above, and Q is carbonyl or dialkoxymethylene. Hydrogenation produces the corresponding 6,9-oxido-9,10-seco-1,3,5(10)-estratrienes and 9-oxy-9,10-seco-1,3,5(10)-estratrienes.

14 Claims, No Drawings

PROCESS FOR THE PREPARATION OF 9,10-SECOESTRANE DERIVATIVES

BACKGROUND OF THE INVENTION

This invention relates to a process for the preparation of 9,10-secoestrane derivatives.

SUMMARY OF THE INVENTION

According to this invention, 9,10-secoestranes of the general Formula

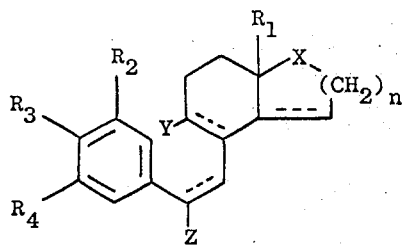

I wherein $n$ is the integer 1 or 2; $R_1$ is lower alkyl; $R_2$, $R_3$ and $R_4$ are alike or different and each are a hydrogen atom, alkoxy or acyloxy; X is free or ketalized carbonyl or free, esterified or etherified hydroxymethylene; Y is a hydroxy group; and Z is a hydrogen atom, or Y and Z collectively are —O—, i.e., with the 6 and 9 carbon atoms form an oxido group, and ▭ each are a single bond or, when Y and Z are oxido, a single or double bond, are produced by cyclizing a compound of the general Formula II

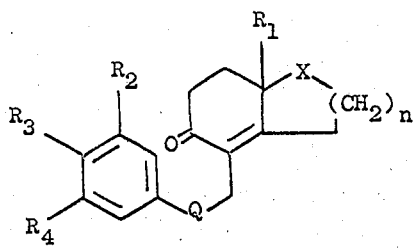

II wherein $n$, $R_1$, $R_2$, $R_3$, $R_4$ and X have the values given above and Q is carbonyl or dialkoxymethylene or like ketalized carbonyl group, in the presence of an acidic catalyst, to produce the 6,9-oxido-9,10-seco-1,3,5(10),6,8,14-estrahexaenes of the general Formula I, i.e., Y and Z collectively are —O— and ▭ are double bonds, which compounds by hydrogenation with hydrogen in the presence of a hydrogenation catalyst, are converted to the 6,9-oxido- and the 9-oxy-9,10-seco-1,3,5(10)-estratrienes of the general Formula I, i.e., Y is OH and Z is H or Y and Z collectively are —O— and ▭ are single bonds. Optionally, a free 17-keto group present in the thus-produced products can be reduced to a hydroxymethylene group and/or ester groups hydrolyzed to free hydroxy groups.

In its composition aspect, this invention relates to the thus-produced 9,10-secoestrane derivatives of the general Formula Ia

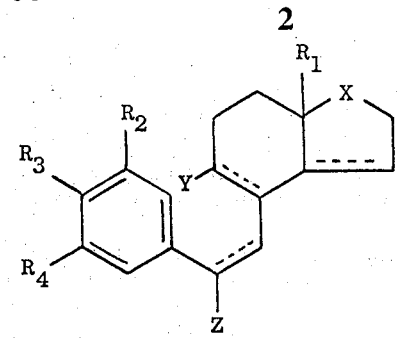

Ia wherein $R_1$, $R_2$, $R_3$, $R_4$, X, Y and Z have the same values as in Formula I.

DETAILED DISCUSSION

Preferred compounds of Formula I are those wherein
a. $n$ is 1 (Compounds of Formula Ia);
b. $R_1$ is methyl or ethyl, especially those of (a);
c. At least one of $R_2$, $R_3$ and $R_4$, preferably $R_4$, is an esterified or etherified hydroxy, e.g., alkanoyloxy of 2–8 carbon atoms or alkoxy of 1–8 carbon atoms, and at least one and preferably both of the remainder are hydrogen atoms, especially those of (a) and (b);
d. X is hydroxymethylene or alkoxymethylene of 1–8 carbon atoms, preferably tert.-butoxymethylene, especially those of (a), (b) and (c).

Lower alkyl means alkyl of 1 to 6 carbon atoms. Preferred $R_1$ groups are those of 1–4 carbon atoms, e.g., methyl, ethyl, propyl, isopropyl and the butyl groups, especially methyl or ethyl.

$R_2$, $R_3$ and $R_4$ can be a hydrogen atom, an alkoxy group or an acyloxy group. Preferred such alkoxy groups are those of 1–4 carbon atoms, e.g., methoxy, ethoxy, propoxy, isopropoxy, butoxy and tert.-butoxy. Preferred such acyloxy groups are those of 1–12 carbon atoms wherein the acyl group is that of an aliphatic, cycloaliphatic or aromatic, preferably hydrocarbon, e.g., carboxylic acid, of 2–8 carbon atoms. Examples of such acyloxy groups are the acetoxy, propionyloxy, butyryloxy, trimethylacetoxy, hexanoyloxy or other alkanoyloxy, cyclopentylcarboxy or benzoyloxy group.

X can be a free or ketalized carbonyl or hydroxymethylene, which can be free, esterified or etherified, e.g., hydroxymethylene, hydrocarbonoxymethylene or hydrocarboncarbonyloxymethylene. Such ketalized carbonyl groups are dialkoxymethylene as defined for Y or preferably alkylenedioxymethylene groups of 2–6 carbon atoms and with 2–3 carbon atoms in the alkylene chain or a o-phenylenedioxymethylene group, e.g., 1,2-ethylenedioxymethylene, 1,3-propylenedioxymethylene, 2,3-butylenedioxymethylene, 2′,2′-dimethyl-1′,3′-propylenedioxymethylene, 2,4-pentylenedioxymethylene and 1,2-phenylenedioxymethylene. Examples of esterified hydroxymethylene groups are those wherein the ester groups have 1–10 carbon atoms, e.g., carboxylic acid groups, preferably hydrocarbon carboxylic acid ester groups, for example, acetoxy, propionyloxy, butyryloxy, trimethylacetoxy, pentanoyloxy, hexanoyloxy, heptanoyloxy, octanoyloxy and benzoyloxy. Examples of etherified hydroxymethylene groups are alkoxymethylene groups of 1–10 carbon atoms and aralkoxymethylene groups of 7–10 carbon atoms in the alkoxy and aralkoxy group, respectively; e.g., methoxy, ethoxy, propoxy, butoxy, tert.-butoxy, isopropoxy and benzyloxy.

As will be apparent to those skilled in the art, if the compounds of Formula I are to be used as intermediates for the production of steroids, when X is a free, esterified or etherified hydroxymethylene group, the oxy group is preferably of the 17β-stereo configuration, corresponding to the 17β-hydroxy group of a naturally occurring steroid.

In the secoestrane derivatives of general Formula II employed as the starting compounds, Q is a carbonyl (C=O) or dialkoxymethylene, e.g., wherein the alkoxy groups each are of 1–4 carbon atoms, for example, dimethoxymethylene, the diethoxymethylene and dibutoxymethylene.

It will be apparent to those skilled in the art that the ether and ester groups of X, $R_1$, $R_2$, $R_3$, and $R_4$ and the ketal group of X are preferably simple and otherwise unsubstituted groups, since more complicated groups are ordinarily of little if any benefit, particularly since most of these groups are merely blocking groups which are subsequently removed to regenerate the free hydroxy or keto group. Therefore, in addition to those $R_2$, $R_3$, $R_4$, X and Y groups more precisely defined in the claims hereinafter, equivalent are those bearing one, two, three or more substituents, e.g., halo, nitro, amido, carbamide, primary, sec. or tert.-amino, alkoxy, alkanoyloxy, mercapto, sulfato, etc.; the cyclic counterparts of alkyl groups, e.g., cyclopropyl, cyclopentyl, cyclohexyl, cycloheptyl; aryl analogs of phenyl groups, e.g., naphthyl, p-tolyl, sym.-xylyl; and sulfonic ester analogs of carboxylic ester groups, e.g., methanesulfonyloxy, ethanesulfonyloxy, p-toluenesulfonyloxy and benzenesulfonyloxy.

In addition to the species of the examples hereinafter, the following are illustrative examples of the compounds of this invention:

3,17β-diacetoxy-6,9-oxido-9,10-seco-1,3,5(10),6,8,14-estrahexaene, 3-benzyloxy-17β-tert.-butyloxy-6,9-oxido-9,10-seco-1,3,5(10), 6,8,14-estrahexaene, 1,3-dimethoxy-17β-benzoyloxy-6,9-oxido-9,10-seco-1,3,5(10), 6,8,14-estrahexaene, 2,3-dimethoxy-17β-benzoyloxy-6,9-oxido-9,10-seco-1,3,5(10), 6,8,14-estrahexaene, 3-methoxy-17,17-(2',2'-dimethyl-propylen-dioxy)-6,9-oxido-9,10-seco-1,3,5(10),6,8,14-estrahexaene, 3,17β-diacetoxy-6,9-oxido-9,10-seco-1,3,5(10)-estratriene, 1,3-dimethoxy-17β-benzoyloxy-6,9-oxido-9,10-seco-1,3,5(10)-estratriene, and 3-methoxy-17,17-(2',2'-dimethyl-propylene-dioxy)-9,10-seco-1,3,5(10)-estratriene-9-ol.

The cyclization of the starting compounds of general Formula II to form a 6,9-oxido group is accomplished with an acidic catalyst. Examples of such catalysts are strongly dissociating carboxylic acids and phenols, e.g., formic acid, acetic acid, nonofluoroacetic acid, trichloroacetic acid, oxalic acid, malonic acid, p-nitrophenol, 2,4-dinitrophenol and 2,4,6-trinitrophenol.

Especially suitable acidic catalysts for the cyclization are mineral acids, sulfonic acid and Lewis acids, such as, for example, hydrogen chloride, sulfuric acid, phosphoric acid, perchloric acid, methanesulfonic acid, benzenesulfonic acid, p-toluenesulfonic acid or boron trifluoride.

The acidic catalysts utilized for the cyclization are preferably employed in catalytic amounts, e.g., 0.1 mole to 0.001 mole of acidic catalyst per mole of starting compound.

The cyclization is preferably conducted in an aprotic solvent, for example, ethers, including diethyl ether, diisopropyl ether, di-n-butyl ether, tetrahydrofuran, anisole, and dimethoxyethane; hydrocarbons, e.g., hexane, cyclohexane, benzene, toluene and xylene; and chlorinated hydrocarbons, e.g., carbon tetrachloride, chloroform, tetrachloroethene, 1,2-dichloroethane and chlorobenzene. However, it is also possible to use as the solvent alcohols such as, for example, methanol, ethanol, n-propanol and n-butanol.

When conducting the cyclization step, it is desirable to remove the alcohol utilized as the solvent or liberated during the cyclization by means of atmospheric or vacuum distillation from the reaction mixture.

If the starting compounds of general Formula II contain, in the 17-position, ester or ether groups which can be readily split off in the presence of water or alcohol and acids, these may be hydrolyzed during the cyclization.

To avoid splitting off of such groups, it is advantageous to conduct the cyclization in the presence of a water-binding agent. For example, when 17β-alkyloxy compounds are employed as the starting materials, suitable water-binding agents include orthoformic acid esters and dialkyl ketals of aliphatic and cycloaliphatic ketones. When 17β-acyloxy compounds are used as the starting compounds, it is also possible, for example, to utilize an acid anhydride corresponding to the 17β-acyloxy groups as the water-binding agents. In the latter case, it is also possible to use the corresponding 17β-hydroxy compounds as the starting substances and to simultaneously acylate and cyclize same by reaction with the acid and acid anhydride in one step.

The cyclization can be effected both at low temperatures, e.g., down to about 0° C., and elevated temperatures, e.g., up to about 150° C. Preferably, the cyclization takes place at a reaction temperature of about 80°–120° C.

It is surprising that the compounds of Formula II, under the conditions of the process of this invention, are cyclized to compounds of Formula I, since previous attempts to cyclize compounds of Formula II to compounds of Formula I were unsuccessful. See Recueil, 89, 1970, 956–960.

A 17-keto group present in the cyclization products can optionally thereafter be reduced to a 17β-hydroxy group in a conventional procedure. This reduction can be carried out, for example, with complex metal hydrides, e.g., sodium borohydride, lithium tri-tert.-butoxyaluminohydride and diisobutyl aluminum hydride. It is also possible, for example, to use the Meerwein-Ponndorf reaction for the reduction by reacting the ketones of Formula I with a secondary alcohol, such as, for example, isopropanol, in the presence of an aluminum alcoholate, e.g., aluminum isopropylate. The aforementioned reactants are suitable particularly for the production of those compounds of Formula I wherein the thus-formed hydroxy group is in the β-position.

The 6,9-oxido-9,10-seco-1,3,5(10),6,8,14-estrahexaenes of the general Formula I can optionally be hydrogenated to the 6,9-oxido- and 9-hydroxy-9,10-seco-1,3,5(10)-estratrienes of Formula I. This hydrogenation is preferably conducted with catalytically activated hydrogen. Heavy metal catalysts are especially well suitable as the catalysts, e.g., Raney nickel, palladium, rhodium and platinum oxide catalysts. When using as the starting compounds for the hydrogenation those 9,10-secoestrane derivatives of general Formula I wherein X is a free, esterified, or etherified hydroxymethylene group, surprisingly only those 9,10-secoestrane derivatives are formed wherein the hydrogen atom entering at the carbon atom in the 14-position is in an α-position orientation.

The hydrogenation can be accomplished in the solvents customarily employed for hydrogenation reactions, e.g., lower alcohols, including methanol, ethanol or isopropanol; esters, e.g., ethyl acetate; and others, e.g., glycol dimethyl ether, dioxane and tetrahydrofuran.

During the hydrogenation, those compounds of general Formula I are primarily produced wherein the lingages ═══ are single bonds, and the substituents Y and Z together are an oxido oxygen atom (—O—). If it is desired to produce these compounds, then it is advantageous to effect the hydrogenation under normal pressure until the theoretical amount of hydrogen has been added. When the hydrogenation period is prolonged or when the hydrogenation is carried out under elevated pressure, the 6,9-oxido ring of the compounds is opened, thus obtaining the compounds of Formula I wherein Z is a hydrogen atom and Y is a hydroxy group.

The compounds produced according to the process of this invention are valuable intermediates. They are particularly suitable for producing pharmacologically effective steroids by means of total synthesis.

Thus, it is possible to convert the 9,10-seco-1,3,5(10)-estratrienes of the general Formula I into the corresponding 9-keto compounds by reaction with chromosulfuric acid is acetone at −10° to 0° C. These 9-keto compounds can be converted in a conventional manner to pharmacologically effective steroids, e.g., by cyclising the 9-keto compounds to the corresponding estrane derivatives, optionally hydrolysing the estrane-esters and estrane-ethers and oxydising the 17β-hydroxyestrane-derivatives under the conventional conditions (German Pat. specification No. 1,231,699).

The compounds of the general formula I may be used as intermediates for the production of pharmacologically active estrane derivatives e.g., of estrone, estradiole, 1-hydroxyestradiole (Arzeneimittel-Forschung 16, 1966, 1518), 2-hydroxyestrone (Steroids 4, 1964,267) or 3-desoxy-estrone (U.S. Pat. No. 3,081,316).

The starting compounds for the process of the present invention can be produced according to the following scheme:

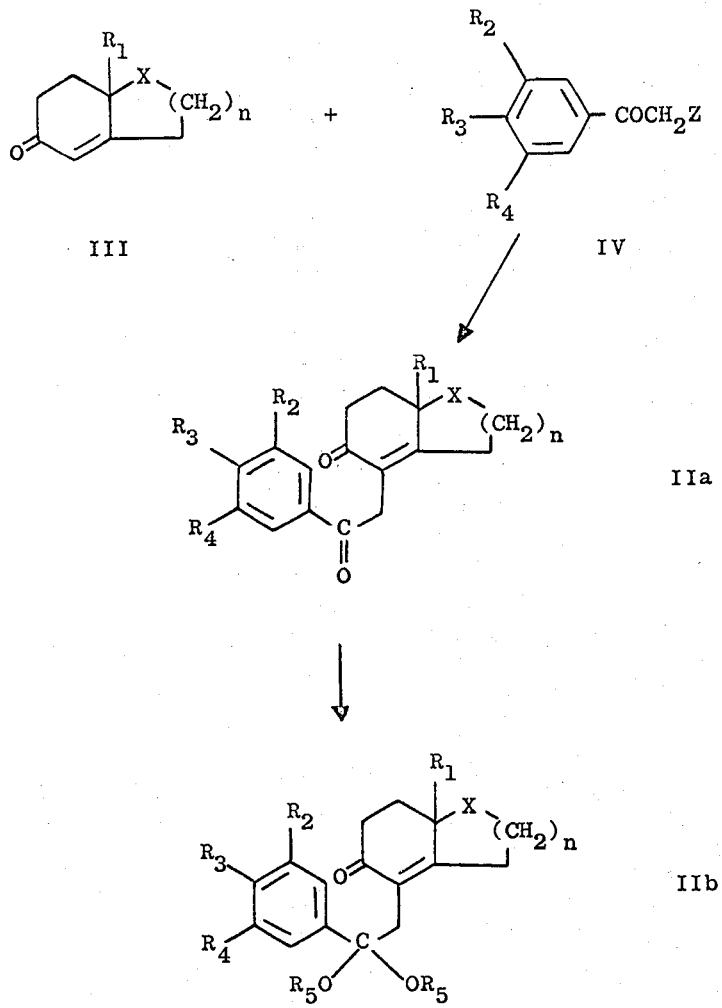

In the above formulae, $R_1$, $R_2$, $R_3$, $R_4$, X and n have the values given above; Z is Cl, Br or I and $R_5$ is lower alkyl, as disclosed in our copending application Ser. No. 409,235, filed Oct. 24, 1973, whose disclosure is incorporated by reference.

Thus, the compounds of Formula III can be reacted, for example, in tetrahydrofuran with sodium hydride and an ω-chloro, ω-bromo- or ω-iodoacetophenone of Formula IV, thus producing the compounds of Formula IIa. The latter can be converted into 6-ketals of the general Formula IIb by reaction with a lower alcohol and a formic acid trialkyl ester in the presence of p-toluenesulfonic acid.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1 a. 20 g. of 1β-tert.-butoxy-7aβ-methyl-5,6,7,7a-tetrahydroindan-5-one is dissolved in 250 ml. of absolute tetrahydrofuran. The reaction flask is then purged with argon. After adding 2.35 g. of sodium hydride, the reaction mixture is refluxed for 10 hours, cooled to −10° C., and combined dropwise with a solution of 22.5 g. of 3'-methoxy-1-bromoacetophenone in 100 ml. of absolute tetrahydrofuran.

After a reaction time of 16 hours at −10° to 0° C., the solvent is distilled off under vacuum, and the reaction mixture is extracted with ether after adding 250 ml. of saturated sodium chloride solution. The ether extract is washed, dried, and concentrated under vacuum. The residue is purified by means of chromatography, recrystallized from diisopropyl ether, and the product is 25.1 g. of 3-methoxy-17β-tert.-butoxy-9,10-seco-1,3,5(10),8(14)-estratetraene-6,9-dione, m.p. 75° – 76.5° C. $[\alpha]_D^{20} = -0.9°$ (chloroform; $c = 1$).

b. 10 g. of 3-methoxy-17β-tert.-butoxy-9,10-seco-1,3,5(10),8(14)-estratetraene-6,9-dione is dissolved in 100 ml. of absolute methanol and 10 ml. of trimethyl orthoformate, and the solution is cooled to 0° C. Then, 50 mg. of p-toluenesulfonic acid is added thereto and the mixture stirred for 20 hours under ice cooling. Subsequently, the reaction mixture is poured into 500 ml. of dilute sodium bicarbonate solution and extracted with ether. The ether phase is washed, dried, and concentrated under vacuum, thus obtaining 12.3 g. of 3,6,6-trimethoxy-17β-tert.-butoxy-9,10-seco-1,3,5(101,8(14)-estratetraen-9-one as a colorless oil. IR band at 6.04 μ; no band at 5.96 μ.

c. 11.9 g. of 3,6,6-trimethoxy-17β-tert.-butoxy-9,10-seco-1,3,5(10),8(14)-estratetraen-9-one is dissolved in 250 ml. of absolute benzene, and 20 mg. of anhydrous p-toluenesulfonic acid is added thereto. Thereafter, the mixture is refluxed, withdrawing 150 ml. of distillate within 2 hours.

The cold solution is mixed with 50 ml. of saturated sodium bicarbonate solution, diluted with 200 ml. of benzene, and worked up as usual. The crude product is recrystallized from methanol, thus producing 8.93 g. of 3-methoxy-17β-tert.butoxy-6,9-oxido-9,10-seco-1,3,5(10),6,8,14-estrahexaene, m.p. 74°–76° C. $[\alpha]_D^{21} = +24°$ (chloroform; $c = 1$).

d. 10.8 g. of 3-methoxy-17β-tert.-butoxy-6,9-oxido-9,10-seco-1,3,5(10),6,8,14-estrahexaene is suspended in 250 ml. of absolute methanol and, after adding 1 g. of palladium charcoal (10%), hydrogenated at 30 atmospheres of hydrogen pressure and room temperature for 10 hours. Then, the reaction product is filtered off from the catalyst, and the solvent is distilled off under vacuum. The residue is recrystallized from diisopropyl ether, thus obtaining 7.8 g. of 3-methoxy-17β-tert.-butoxy-9,10-seco-1,3,5(10)-estratrien-9-ol, m.p. 102°–103° C. $[\alpha]_D^{21} = +56°$ (chloroform; $c = 1$).

e. 3.6 g. of 3-methoxy-17β-tert.-butoxy-9,10-seco-1,3,5(10)-estratrien-9-ol is dissolved in 70 ml. of absolute acetone and then cooled to −5° C. Under agitation, 2.6 ml. of an 8N solution of chromic acid in sulfuric acid (Jones reagent) is added thereto within 5 minutes dropwise, and the reaction mixture is stirred for 20 minutes at 0° C. The mixture is then worked up as usual, obtaining 3.49 g. of 3-methoxy-17β-tert.butoxy-9,10-seco-1,3,5(10)-estratrien-9-one as a colorless oil. IR band at 5.86 μ. $[\alpha]_D^{25} = +27.5°$ (chloroform; $c = 1$).

EXAMPLE 2 a. 3.2 g. of 3-methoxy-17β-tert.-butoxy-9,10-seco-1,3,5(10),8(14)-estratetraene-6,9-dione is reacted, as described in Example 1(b), with 3.2 ml. of trimethyl orthoformate and 30 ml. of absolute methanol in the presence of 20 mg. of p-toluenesulfonic acid, and the reaction mixture is concentrated under vacuum after termination of the reaction. The thus-obtained residue is dissolved in 100 ml. of absolute benzene and refluxed for 3 hours while withdrawing 50 ml. of distillate. The reaction mixture is worked up as described in Example 1(c), thus producing 2.43 g. of 3-methoxy-17β-tert.-butoxy-6,9-oxido-9,10-seco-1,3,5(10),6,8,14-estrahexaene, m.p. 75°–77° C.

b. 1.9 g. of 3-methoxy-17β-tert.-butoxy-6,9-oxido-9,10-seco-1,3,5(10),6,8,14-estrahexaene is dissolved in 25 ml. of ethanol; after adding 150 mg. of palladium/charcoal (10%), the reaction mixture is hydrogenated under normal pressure and at room temperature. Within 5 hours, 375 ml. of hydrogen is absorbed. Then, the catalyst is filtered off, the solution is concentrated under vacuum, and the product is 1.85 g. of 3-methoxy-17β-tert.-butoxy-6,9-oxido-9,10-seco-1,3,5(10)-estratriene.

EXAMPLE 3

1.3 g. of 3-methoxy-17β-tert.-butoxy-9,10-seco-1,3,5(10),8(14)-estratetraene-6,9-dione is mixed with 20 ml. of toluene and 50 mg. of p-toluenesulfonic acid and heated for 18 hours on a water trap. Then, the reaction mixture is combined with 10 ml. of sodium bicarbonate solution, diluted with 50 ml. of benzene, and the organic phase is separated. The latter is worked up as usual, thus obtaining 0.825 g. of 3-methoxy-6,9-oxido-9,10-seco-1,3,5(10),6,8,14-estrahexaen-17β-ol as a colorless oil.

EXAMPLE 4 a. 11.3 g. of 1β-tert.-butoxy-7aβ-ethyl-5,6,7,7a-tetrahydroindan-5-one is reacted according to Example 1 in 150 ml. of absolute dimethoxyethane with 1.3 g. of sodium hydride. With ice cooling, a solution of 12.4 g. of 3'-methoxy-1-bromoacetophenone in 50 ml. of absolute dimethoxyethane is added dropwise within 10 minutes to the reaction mixture, and the latter is then stirred for 16 hours under ice cooling.

The reaction mixture is worked up and purified in accordance with the mode of operation described in Example 1(a), thus obtaining 11.9 g. of 3-methoxy-17β-tert.-butoxy-18-methyl-9,10-seco-1,3,5(10),8(14)-estratetraene-6,9-dione as a colorless oil. IR bands at 5.96 μ and 6.05 μ. $[\alpha]_D^{21} = -0.2°$ (chloroform; $c = 1$).

b. 11.1 g. of 3-methoxy-17β-tert.-butoxy-18-methyl-9,10-seco-1,3,5(10),8(14)-estratetraene-6,9-dione is reacted as described in Example 2(a), thus producing 9.8 g. of 3-methoxy-17β-tert.-butoxy-6,9-oxido-18-methyl-9,10-seco-1,3,5(10),6,8,14-estrahexaene, m.p. 83° – 84.5° C. $[\alpha]_D^{21} = +16.9°$ (chloroform; $c = 1$).

c. 5.6 g. of 3-methoxy-17β-tert.-butoxy-6,9-oxido-18-methyl-9,10-seco-1,3,5(10),6,8,14-estrahexaene is hydrogenated as described in Example 1(d), thus obtaining 5.3 g. of 3-methoxy-17β-tert.-butoxy-18-methyl-9,10-seco-1,3,5(10)-estratrien-9-ol as a colorless oil. This compound is oxidizable, under the conditions described in Example 1(e), to produce 3-methoxy-17β-tert.-butoxy-18-methyl-9,10-seco-1,3,5(10)-estratrien-9-one.

EXAMPLE 5 a. 5.3 g. of 1β-tert.-butoxy-7aβ-methyl-5,6,7,7a-tetrahydroindan-5-one is reacted with sodium hydride in tetrahydrofuran and subsequently with ω-bromoacetophenone, as described in Examine 1(a), and worked up. The product is 5.85 g. of 17β-tert.-butoxy-9,10-seco-1,3,5(10),8(14)-estratetraene-6,9-dione, m.p. 86° – 87.5° C. $[\alpha]_D^{21} = -0.5°$ (chloroform; $c = 1$).

b. 17β-tert.-Butoxy-9,10-seco-1,3,5(10),8(14)-estratetraene-6,9-dione is reacted and worked up as described in Example 2(a). The thus-obtained crude product is recrystallized from methanol, thus producing 17β-tert.-butoxy-6,9-oxido-9,10-seco-1,3,5(10),6,8,14-estrahexaene, m.p. 97°–98°C. $[\alpha]_D^{21} = -67.7°$ (chloroform; $c = 1$).

c. 17β-tert.-butoxy-6,9-oxido-9,10-seco-1,3,5(10),6,8,14-estrahexaene is hydrogenated under the conditions described in Example 1(d), thus obtaining 17β-tert.-butoxy-9,10-seco-1,3,5(10)-estratrien-9-ol as a colorless oil. $[\alpha]_D^{22} = +35.2°$ (chloroform; $c = 1$). This compound can be oxidized under the conditions described in Example 1(e) to 17β-tert.-butoxy-9,10-seco-1,3,5(10)-estratrien-9-one. $[\alpha]_D^{22} = +21.7°$ (chloroform; $c = 1$).

EXAMPLE 6 a. 10 g. of 1β-hydroxy-7aβ-methyl-5,6,7,7a-tetrahydroindan-5-one is dissolved in 100 ml. of absolute dimethoxy-ethane, and 6 g. of freshly distilled ethylvinyl ether and 10 mg. of p-toluenesulfonic acid are added thereto. The mixture is agitated for one hour at room temperature. Then, the excess of ethylvinyl ether is distilled off under vacuum and 1.7 g. of sodium hydride is added. After a reaction time of 15 hours at 70° C., the reaction mixture is cooled to −5° C. and, with 20 minutes, a solution of 16.5 g. of 3′-methoxy-1-bromoacetophenone in 50 ml. of absolute dimethoxy-ethane is added dropwise. After a reaction period of 16 hours under ice cooling, the mixture is gently acidified to pH 3 with 1N hydrochloric acid and agitated for 30 minutes at room temperature.

The light-brown crude product obtained after the usual working-up steps is chromatographed on a silica gel column for purification purposes, thus producing 15.8 g. of 17β-hydroxy-3-methoxy-9,10-seco-1,3,5(10),8(14)-estratetraene-6,9-dione as a colorless oil. IR bands at 5.95 μ and 6.02 μ. $[\alpha]_D^{21} = +13.5°$ (chloroform; $c = 1$).

b. 1 g. of 17β-hydroxy-3-methoxy-9,10-seco-1,3,5(10),8(14)-estratetraene-6,9-dione is dissolved in 10 ml. of absolute benzene and 0.7 ml. of 2,2-dimethoxypropane, combined with 10 mg. of p-toluenesulfonic acid, refluxed for 4 hours. Then, the solution is allowed to cool down, mixed with saturated sodium bicarbonate solution, the mixture is worked up as described in Example 3, and the product is 0.846 g. of 3-methoxy-6,9-oxido-9,10-seco-1,3,5(10),6,8,14-estrahexaen-17β-ol as a colorless oil.

c. 3.15 g. of 3-methoxy-6,9-oxido-9,10-seco-1,3,5(10),6,8,14-estrahexaen-17β-ol is hydrogenated as described in Example 1(d), thus obtaining, after recrystallization from diisopropyl ether, 2.85 g. of 3-methoxy-9,10-seco-1,3,5(10)-estratriene-9,17β-diol, m.p. 100°–103° C. $[\alpha]_D^{21} = +34.34°$ (chloroform; $c = 1$).

This compound can be oxidized under the conditions described in Example 1(e) to obtain 3-methoxy-9,10-seco-1,3,5(10)-estratriene-9,17-dione. $[\alpha]_D^{22} = +79.6°$ (chloroform; $c = 1$).

EXAMPLE 7 a. 4.6 g. of 1β-hydroxy-7aβ-ethyl-5,6,7,7a-tetrahydroindan-5-one is reacted in 60 ml. of absolute dimethoxyethane in the manner described in Example 6(a) first with vinylethyl ether and then with sodium hydride. Under ice cooling and stirring, 7.9 g. of 3′-methoxy-1-bromoacetophenone in 30 ml. of absolute dimethoxyethane is added dropwise within 10 minutes, and the mixture is allowed to stand for 16 hours under ice cooling. Then, the reaction mixture is acidified to pH 3 with 1N hydrochloric acid and worked up as described in Example 6(a), thus obtaining 6.1 g. of 17β-hydroxy-3-methoxy-18-methyl-9,10-seco-1,3,5(10),8(14)-estratetraene-6,9-dione as a colorless oil. IR bands at 5.96 μ and 6.04 μ. $[\alpha]_D^{21} = +9.2°$ (chloroform; $c = 1$).

b. 3.2 g. of 17β-hydroxy-3-methoxy-18-methyl-9,10-seco-1,3,5(10),8(14)-estratetraene-6,9-dione is reacted and worked up as set forth in Example 6(b), thus obtaining 2.73 g. of 3-methoxy-6,9-oxido-18-methyl-9,10-seco-1,3,5(10),6,8,14-estrahexaen-17β-ol as a colorless oil. $[\alpha]_D^{21} = -8.8°$ (chloroform; $c = 1$).

c. 5.7 g. of 3-methoxy-6,9-oxido-18-methyl-9,10-seco-1,3,5(10),6,8,14-estrahexaen-17β-ol is hydrogenated as described in Example 1(d), thus producing 5.2 g. of 3-methoxy-18-methyl-9,10-seco-1,3,5(10)-estratriene-9,17β-diol as a colorless oil.

This compound can be oxidized to 3-methoxy-18-methyl-9,10-seco-1,3,5(10)-estratriene-9,17-dione under the conditions disclosed in Example 1(e). Melting point of this product: 54°–55° C. (hexane).

EXAMPLE 8

1 g. of 3-methoxy-17β-hydroxy-9,10-seco-1,3,5(10),8(14)-estratetraene-6,9-dione is mixed with 20 ml. of absolute benzene, 1.5 ml. of acetic anhydride, and 10 mg. of p-toluenesulfonic acid and refluxed for 8 hours. The reaction mixture is worked up as set forth in Example 6(b), thus producing 720 mg. of 3-methoxy-17β-acetoxy-6,9-oxido-9,10-seco-1,3,5(10),6,8,14-estrahexaene. IR bands at 5.78 μ and 6.1 μ.

EXAMPLE 9 a. 1β-Tert.-butyloxy-7aβ-methyl-5,6,7,7a-tetrahydroindan-5-one can be condensed with 3,5-dimethoxy-1-bromo-acetophenone in the manner described in Example 1(a) to give 1,3-dimethoxy-17β-tert.-butyloxy-9,10-seco-1,3,5(10),8(14)-estratetraene-6,9-dione which can be ketalised under the conditions of Example 1(b) to the 1,3,6,6-tetramethoxy-17β-tert.-butyloxy-9,10-seco-1,3,5(10),8(14)-estratetraene-9-one.

b. The 1,3,6,6-tetramethoxy-17β-tert.-butyloxy-9,10-seco-1,3,5(10),8(14)-estratetraene-9-one is reacted as described in Example 1(c), thus producing the 1,3-dimethoxy-17β-tert.-butyloxy-6,9-oxido-9,10-seco-1,3,5(10),6,8,14-estrahexaene which can be hydrogenated under the conditions described in Example 1(d) to obtain 1,3-dimethoxy-17β-tert.-butyloxy-9,10-seco-1,3,5(10)-estratriene-9-ol.

EXAMPLE 10 a. 1β-Tert.-butyloxy-7aβ-methyl-5,6,7,7a-tetrahydroindan-5-one can be condensed with 4,5-dimethoxy-1-bromo-acetophenone in the manner described in Example 1(a) to give 1,3-dimethoxy-17β-tert.-butyloxy-9,10-seco-1,3,5(10),8(14)-estratetraene-6,9-dione which can be ketalised under the conditions of Example 1(b) to give 2,3,6,6-tetramethoxy-17β-tert.-butyloxy-9,10-seco-1,3,5(10),8(14)-estratetraene-9-one.

b. The 2,3,6,6-tetramethoxy-17β-tert.-butyloxy-9,10-seco-1,3,5(10),8(14)-estratetraene-9-one is reacted as described in Example 1(c), thus producing give 2,3-dimethoxy-17β-tert.-butyloxy-6,9-oxido-9,10-seco-1,3,5(10),6,8,14-estrahexaene which can be hydrogenated under the conditions described in Example 1(d) to obtain 2,3-dimethoxy-17β-tert.-butyloxy-9,10-seco-1,3,5(10)-estratriene-9)-ol.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 9,10-seco-1,3,5(10)-estratriene-9-ol derivative of the formula

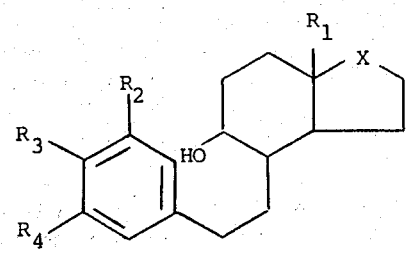

wherein $R_1$ is alkyl of 1–6 carbon atoms; $R_2$, $R_3$ and $R_4$ are each hydrogen or alkoxy of 1–8 carbon atoms; and X is hydroxymethylene; alkoxymethylene wherein the alkoxy group contains 1–10 carbon atoms; dialkoxymethylene wherein the alkoxy groups each contain 1–4 carbon atoms; or hydrocarbon aralkoxymethylene wherein the aralkoxy group contains 7–10 carbon atoms.

2. A compound according to claim 1, wherein $R_1$ is methyl or ethyl.

3. A compound according to claim 1, wherein at least one of $R_2$, $R_3$ and $R_4$ is alkoxy of 1–8 carbon atoms and at least one of the remainder of $R_2$, $R_3$ and $R_4$ is hydrogen.

4. A compound according to claim 3, wherein $R_4$ is alkoxy of 1–8 carbon atoms and $R_2$ and $R_3$ are both hydrogen.

5. A compound according to claim 1 wherein X is hydroxymethylene or t-butoxymethylene.

6. A compound according to claim 1, wherein X is hydroxymethylene or alkoxymethylene wherein alkoxy is of 1–8 carbon atoms.

7. A compound according to claim 6 wherein $R_1$ is methyl or ethyl; $R_2$ and $R_3$ are both hydrogen; and $R_4$ is alkoxy of 1–4 carbon atoms.

8. The compound of claim 1, 3-methoxy-17β-tert.-butoxy-9,10-seco-1,3,5(10)-estratriene-9-ol.

9. The compound of claim 1, 3-methoxy-17β-tert.-butoxy-18-methyl-9,10-seco-1,3,5(10)-estratriene-9-ol.

10. The compound of claim 1, 17β-tert.-butoxy-9,10-seco-1,3,5(10)-estratriene-9-ol.

11. The compound of claim 1, 3-methoxy-9,10-seco-1,3,5(10)-estratriene-9,17β-diol.

12. The compound of claim 1, 3-methoxy-18-methyl-9,10-seco-1,3,5(10)-estratriene-9,17β-diol.

13. A process for preparing a compound according to claim 1, which comprises hydrogenating with catalytically activated hydrogen a starting compound of the formula

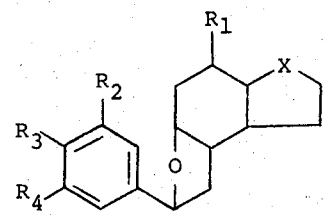

wherein $R_1$, $R_2$, $R_3$, $R_4$ and X have the above-indicated values, under a sufficiently prolonged hydrogenation period or a sufficiently elevated pressure to open the 6,9-oxide ring of the starting compound and form said product.

14. A process according to claim 13 wherein said starting compound is formed in situ by hydrogenating with catalytically activated hydrogen a starting compound of the formula

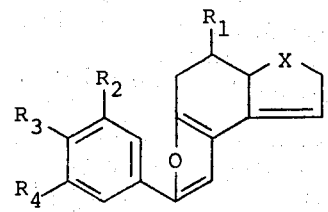

wherein $R_1$, $R_2$, $R_3$, $R_4$ and X have the above-indicated values.

* * * * *